(12) United States Patent
Kondo

(10) Patent No.: US 12,340,672 B2
(45) Date of Patent: Jun. 24, 2025

(54) HEALTH STATUS DETERMINATION SYSTEM, RESIDENCE, MANAGEMENT DEVICE, AND HEALTH STATUS DETERMINATION METHOD

(71) Applicant: SEKISUI HOUSE, LTD., Osaka (JP)

(72) Inventor: Masayuki Kondo, Osaka (JP)

(73) Assignee: SEKISUI HOUSE, LTD., Osaka (JP)

(*) Notice: Subject to any disclaimer, the term of this patent is extended or adjusted under 35 U.S.C. 154(b) by 125 days.

(21) Appl. No.: 18/270,530

(22) PCT Filed: Dec. 21, 2021

(86) PCT No.: PCT/JP2021/047168
§ 371 (c)(1),
(2) Date: Jun. 30, 2023

(87) PCT Pub. No.: WO2022/149456
PCT Pub. Date: Jul. 14, 2022

(65) Prior Publication Data
US 2024/0296727 A1 Sep. 5, 2024

(30) Foreign Application Priority Data
Jan. 6, 2021 (JP) .................................. 2021-000835

(51) Int. Cl.
*G08B 21/04* (2006.01)

(52) U.S. Cl.
CPC ..... *G08B 21/0423* (2013.01); *G08B 21/0461* (2013.01)

(58) Field of Classification Search
CPC ........ E21B 47/16; E21B 47/002; E21B 47/09; B06B 1/0633; G01V 1/46; G01V 1/50; G01V 1/52
See application file for complete search history.

(56) References Cited

U.S. PATENT DOCUMENTS

2006/0058704 A1   3/2006   Graichen et al.

FOREIGN PATENT DOCUMENTS

JP          3378540 B2       2/2003
JP       2009-240661 A      10/2009

OTHER PUBLICATIONS

International Search Report (PCT/ISA/210), issued in PCT/JP2021/047168, dated Mar. 15, 2022.

*Primary Examiner* — Brian A Zimmerman
*Assistant Examiner* — Cal J Eustaquio
(74) *Attorney, Agent, or Firm* — Birch, Stewart, Kolasch & Birch, LLP

(57) ABSTRACT

A management device includes a calculation part that calculates, on the basis of first data, second data, and third data acquired by an acquisition part, a period of time consumed by a subject to walk from an uppermost step to a lowermost step of a stair for the first time after the waking, and outputs time data indicative of the period of time, a storage part that stores a plurality of pieces of time data of the past, a determination part that determines a health condition of the subject on a current day on the basis of the time data of the current day and the pieces of time data of the past, and an output part that outputs a determination result of the determination part.

7 Claims, 7 Drawing Sheets

HEALTH STATUS DETERMINATION SYSTEM, RESIDENCE, MANAGEMENT DEVICE, AND HEALTH STATUS DETERMINATION METHOD

TECHNICAL FIELD

The present invention relates to a health condition determination system, management device, and a health condition determination method.

BACKGROUND ART

Patent Literature 1 discloses an anomaly determination device including condition detection means to be worn on a human body of a subject, and determination means wirelessly communicable with the condition detection means. The condition detection means detects various conditional items (a body temperature, a heart rate, a posture, a travelled distance, a sleep state, and the like) of the subject by a plurality of sensors. The determination means determines whether an anomaly occurs in the subject on the basis of the detection results of the condition by the condition detection means.

In the anomaly determination device disclosed in Patent Literature 1, the condition detection means detects various conditional items (a body temperature, a heart rate, a posture, a travelled distance, a sleep state, and the like) of the subject. However, the various conditional items of the subject are liable to widely fluctuate due to a difference between periods of time during which the detection is executed, or a difference between daily activity schedules of the subject. Therefore, the determination of an anomaly of the subject on the basis of detection results of the conditional items, which are likely to fluctuate due to factors having no connection with a health condition, merely provides a result with a low accuracy.

Further, the condition detection means constantly detects various conditional items of the subject and sends them to the determination means. Consequently, the determination means is liable to have an enormous amount of data to be processed, thereby receiving an increased process load.

CITATION LIST

Patent Literature

Patent Literature 1: Japanese Patent No. 3378540

SUMMARY OF INVENTION

The present invention has been made in view of the circumstances described above, and an object thereof is to obtain health condition determination system, management device, and a health condition determination method that provide an improved determination accuracy of a health condition of a subject and require a reduced process load entailed by the determination.

A health condition determination system according to an aspect of the present invention is a health condition determination system for determining a health condition of a subject living in a housing provided with a stair, and includes: a first sensor that detects waking of the subject and outputs first data indicative of a result of the detection; a second sensor that detects the subject staying on one end step of the stair and outputs second data indicative of a result of the detection; a third sensor that detects the subject staying on the other end step of the stair and outputs third data indicative of a result of the detection; and a management device that is communicable with the first sensor, the second sensor, and the third sensor. The management device includes an acquisition part that acquires the first data, the second data, and the third data, a calculation part that calculates, on the basis of the first data, the second data, and the third data acquired by the acquisition part, a period of time consumed for a first walking of the subject after the waking from the one end step to the other end step of the stair, and outputs time data indicative of the period of time, a storage part that stores a plurality of pieces of time data of a past, a determination part that determines a health condition of the subject on a current day on the basis of the time data of the current day and the pieces of time data of the past, and an output part that outputs a determination result of the determination part.

DESCRIPTION OF EMBODIMENTS

Hereinafter, an embodiment of the present invention will be described with reference to the accompanied drawings. Elements allotted with the same sign in different drawings are construed to be the same element or corresponding elements.

Figure 1:
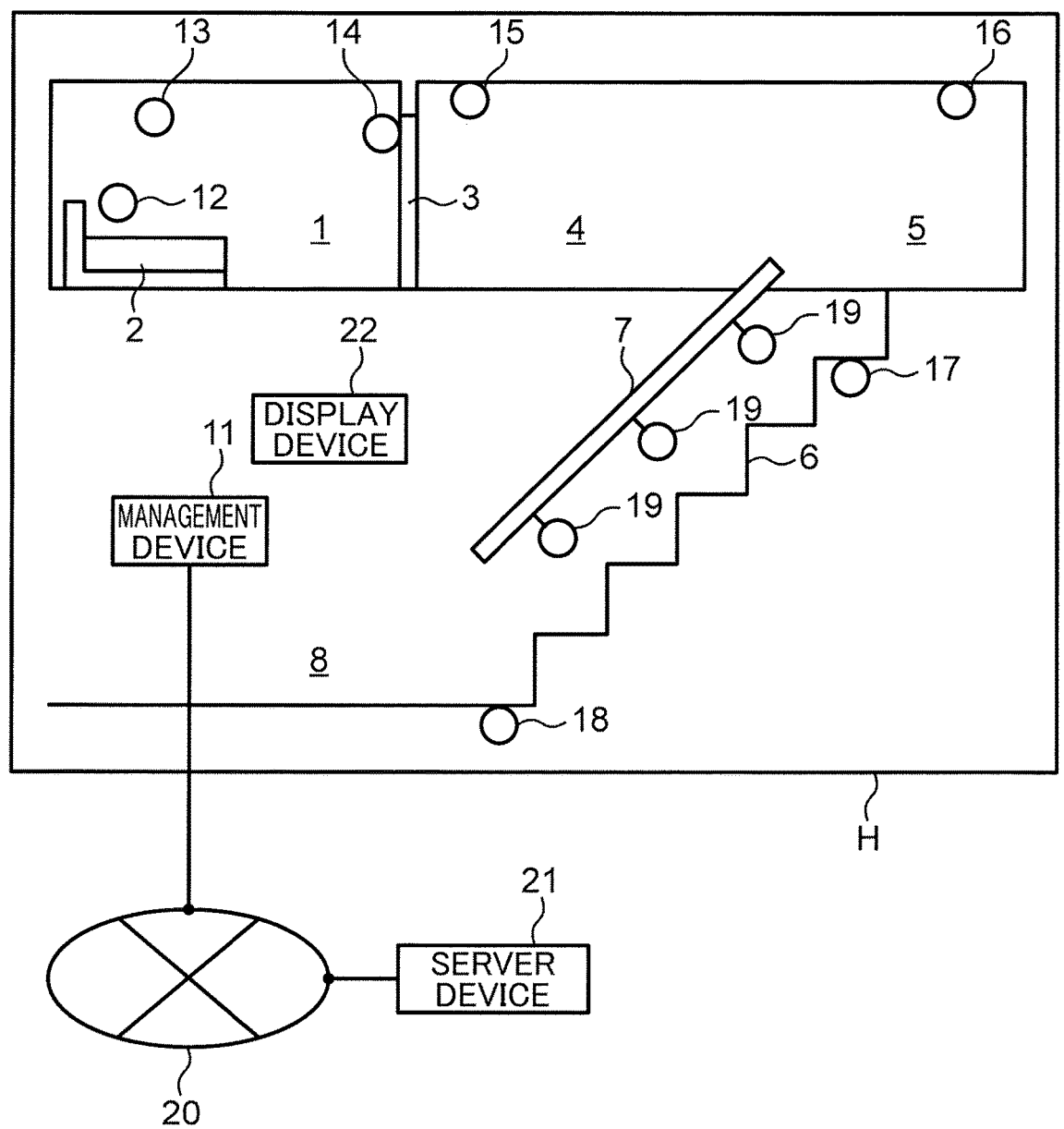
FIG. 1 is a diagram schematically showing a configuration of a health condition determination system according to an embodiment of the present invention.

FIG. 1 is a diagram schematically showing a configuration of a health condition determination system 100 according to an embodiment of the present invention. The health condition determination system 100 is installed in a housing H where a user (hereinafter, referred to as "subject") being a subject of determination of a health condition lives.

In the example of FIG. 1, the housing H is a two-story private house, and includes a corridor 8 and a living room (not shown) connected thereto on a first floor, and a bedroom 1, a corridor 4, and a landing 5 on a second floor. The bedroom 1 is provided with a bed 2 used by the subject when sleeping. A door 3 is provided between the bedroom 1 and the corridor 4. The landing 5 is provided at the end of the corridor 4 viewed from the bedroom 1. The corridor 8 and the landing 5 are connected via a stair 6 including a handrail 7. The bedroom 1 may be defined on the first floor and the living room may be defined on the second floor, or the bedroom 1 may be defined on a basement and the living room may be defined on the first floor.

The health condition determination system 100 includes a waking sensor 12, a bed leaving sensor 13, an open/close sensor 14, human sensing sensors 15, 16, load sensors 17 to 19, and a management device 11. The waking sensor 12, the bed leaving sensor 13, the open/close sensor 14, the human sensing sensors 15, 16, the load sensors 17 to 19, and the management device 11 are mutually communicable via a desired communication way, e.g., Wi-Fi.

The waking sensor 12 is, for example, a sleep meter (e.g., a wristwatch) wearable on a human body of the subject, a sleep meter embedded in a mattress of the bed 2, or a sleep meter provided on a ceiling of the bedroom 1. The waking sensor (a first sensor) 12 detects that the subject wakes up from a sleep lasting a certain period of time (e.g., three hours) or more to thereby detect the waking of the subject. When detecting the waking of the subject, the waking sensor 12 sends waking detection data indicative of the result of the detection to the management device 11.

The bed leaving sensor 13 is, for example, a camera that takes an image of surroundings around the bed 2, or a load sensor embedded in the bed 2. The bed leaving sensor 13 detects that the subject leaves the bed 2. When detecting that the subject leaves the bed, the bed leaving sensor 13 sends bed leaving detection data indicative of the result of the detection to the management device 11.

The open/close sensor 14 is, for example, a magnetic sensor embedded in the door 3. The open/close sensor 14 detects that the door 3 is opened and the door 3 is closed. When detecting the opening/closing of the door 3, the open/close sensor 14 sends open/close detection data indicative of the result of the detection to the management device 11.

The human sensing sensor 15 is provided on a rear side of the door 3 when viewed from the bedroom 1. The human sensing sensor 15 is, for example, an infrared sensor provided on the ceiling, or a load sensor embedded in the floor. The human sensing sensor 15 detects that the subject exits the bedroom 1. When detecting that the subject exits the bedroom 1, the human sensing sensor 15 sends room exiting detection data indicative of the result of the detection to the management device 11.

The human sensing sensor 16 is provided on the landing 5. The human sensing sensor 16 is, for example, an infrared sensor provided on the ceiling, or a load sensor embedded in the floor. The human sensing sensor 16 detects that the subject stays on the landing 5 (i.e., at a position immediately before an uppermost step of the stair 6). When detecting that the subject stays on the landing 5, the human sensing sensor 16 sends location detection data indicative of the result of the detection to the management device 11.

The load sensor 17 is embedded in the uppermost step of the stair 6. The load sensor (the second sensor) 17 detects that the subject stays on the uppermost step of the stair 6. When detecting that the subject stays on the uppermost step of the stair 6, the load sensor 17 sends location detection data indicative of the result of the detection to the management device 11.

The load sensor 18 is embedded in a lowermost step of the stair 6. The load sensor (the third sensor) 18 detects that the subject stays on the lowermost step of the stair 6. When detecting that the subject stays on the lowermost step of the stair 6, the load sensor 18 sends location detection data indicative of the result of the detection to the management device 11.

The load sensor 19 is embedded in a support member via which the handrail 7 is attached to a wall. When a plurality of support members is provided, a load sensor 19 is embedded in each of the support members. The load sensor (the fourth sensor) 19 detects a load applied to the handrail 7 by the subject. When detecting a load applied to the handrail 7 by the subject, the load sensor 19 sends load value data indicative of the detected load value to the management device 11.

The management device 11 is mutually communicable with a display device 22 via a desired communication way, e.g., Wi-Fi. The display device 22 is, for example, a smartphone used by the subject.

The management device 11 is mutually communicable with a server device 21, e.g., a cloud server, via a desired communication network 20, e.g., a public circuit network, using a desired communication protocol, e.g., IP.

Figure 2:
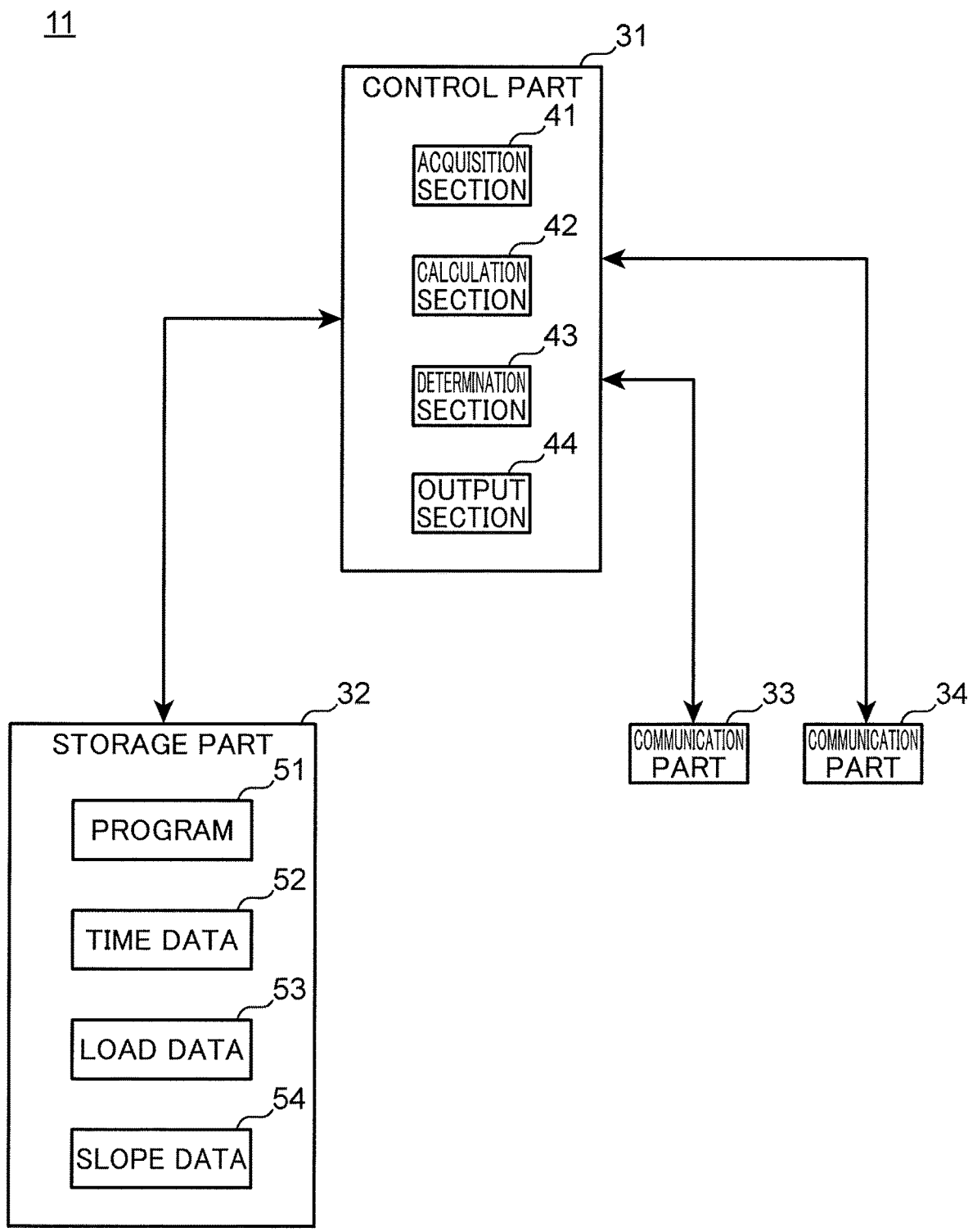
FIG. 2 is a diagram showing a simplified configuration of a management device.

FIG. 2 is a diagram showing a simplified configuration of the management device 11. The management device 11 includes a control part 31, a storage part 32, and communication parts 33, 34.

The control part 31 includes a data processing device, e.g., CPU. The storage part 32 includes a non-volatile storage device, e.g., a hard disk, a semiconductor memory, or the like. The communication part 33 includes a communication module adapted to a desired communication way, e.g., Wi-Fi, to communicate with the waking sensor 12, the bed leaving sensor 13, the open/close sensor 14, the human sensing sensors 15, 16, the load sensors 17 to 19, and the display device 22. The communication part 34 includes a communication module for a desired communication protocol, e.g., IP, to communicate with the server device 21.

The storage part 32 stores a program 51, time data 52, load data 53, and slope data 54.

The CPU implements a program read from the storage part 32 such that the control part 31 functions as an acquisition section 41, a calculation section 42, a determination section 43, and an output section 44. In other words, the program 51 causes a computer, serving as the management device 11, to function as the acquisition section 41, the calculation section 42, the determination section 43, and the output section 44.

Figure 3:
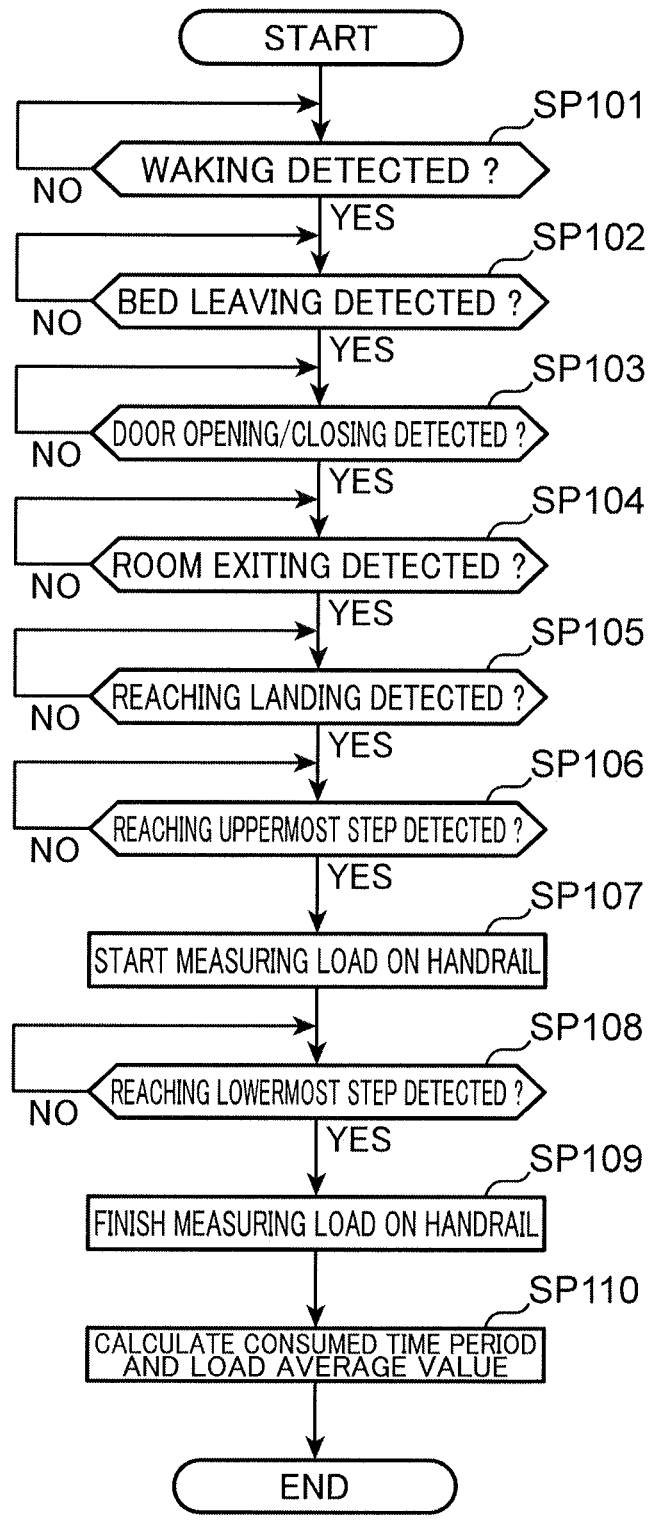
FIG. 3 is a flowchart showing a process executed by a control part to generate time data and load data.

FIG. 3 is a flowchart showing a process executed by the control part 31 to generate time data 52 and load data 53.

First, in Step SP101, when the subject wakes up and the waking sensor 12 sends waking detection data, the communication part 33 receives the waking detection data, and the acquisition section 41 acquires the waking detection data from the communication part 33. The processing of Step SP101 is repeatedly executed until the acquisition section 41 acquires the waking detection data (i.e., until the subject wakes up).

Thereafter, in Step SP102, when the subject leaves the bed and the bed leaving sensor 13 sends bed leaving detection data, the communication part 33 receives the bed leaving detection data, and the acquisition section 41 acquires the bed leaving detection data from the communication part 33. The processing of Step SP102 is repeatedly executed until the acquisition section 41 acquires the bed leaving detection data (i.e., until the subject leaves the bed). When the subject resumes sleeping without leaving the bed, the flow returns to Step SP101.

Subsequently, in Step SP103, when the subject opens or closes the door 3 and the open/close sensor 14 sends open/close detection data, the communication part 33 receives the open/close detection data, and the acquisition section 41 acquires the open/close detection data from the communication part 33. The processing of Step SP103 is repeatedly executed until the acquisition section 41 acquires the open/close detection data (i.e., until the subject opens or closes the door 3). When the subject goes back to bed 2 without opening or closing the door 3, the flow returns to Step SP102.

Thereafter, in Step S104, when the subject exits the bedroom 1 and the human sensing sensor 15 sends room exiting detection data, the communication part 33 receives the room exiting detection data, and the acquisition section 41 acquires the room exiting detection data from the communication part 33. The processing of Step SP104 is repeatedly executed until the acquisition section 41 acquires the room exiting detection data (i.e., until the subject exits the bedroom 1).

Subsequently, in Step SP105, when the subject reaches the landing 5 and the human sensing sensor 16 sends location detection data, the communication part 33 receives the location detection data, and the acquisition section 41 acquires the location detection data from the communication part 33. The processing of Step SP105 is repeatedly executed until the acquisition section 41 acquires the location detection data (i.e., until the subject reaches the landing 5).

Thereafter, in Step SP106, when the subject reaches the uppermost step of the stair 6 and the load sensor 17 sends location detection data, the communication part 33 receives the location detection data, and the acquisition section 41 acquires the location detection data from the communication part 33. The processing of Step SP106 is repeatedly executed until the acquisition section 41 acquires the location detection data (i.e., until the subject reaches the uppermost step of the stair 6).

When the subject reaches the uppermost step of the stair 6, thereafter, in Step SP107, the control part 31 sends a control signal from the communication part 33 to the load sensor 19 to thereby cause the load sensor 19 to start a load measurement. When the load sensor 19 sends load value data, the communication part 33 receives the load value data, and the acquisition section 41 acquires the load value data from the communication part 33.

Subsequently, in Step SP108, when the subject reaches the lowermost step of the stair 6 and the load sensor 18 sends location detection data, the communication part 33 receives the location detection data, and the acquisition section 41 acquires the location detection data from the communication part 33. The processing of Step SP108 is repeatedly executed until the acquisition section 41 acquires the location detection data (i.e., until the subject reaches the lowermost step of the stair 6).

When the subject reaches the lowermost step of the stair 6, subsequently, in Step SP109, the control part 31 sends a control signal from the communication part 33 to the load sensor 19 to thereby cause the load sensor 19 to finish the load measurement.

Thereafter, in Step SP110, the calculation section 42 calculates a time difference between a time when the acquisition section 41 acquires the location detection data sent from the load sensor 17 and a time when the acquisition section 41 acquires the location detection data sent from the load sensor 18 to obtain a period of time (the consumed time period of the current day T0) consumed by the subject to walk from the uppermost step to the lowermost step of the stair 6. The control part 31 generates time data 52 containing the consumed time period and date information, and stores the time data 52 in the storage part 32. The storage part 32 cumulatively stores also a plurality of pieces of time data 52 concerning a plurality of periods of time consumed in the past until the day before. Further, the calculation section 42 calculates a cumulative value of pieces of load value data acquired by the acquisition section 41 during the consumed time period, and divides the cumulative value by the consumed time period to thereby obtain a load average value applied to the handrail 7 by the subject while walking from the uppermost step to the lowermost step of the stair 6 (a load average value of the current day L0). The control part 31 generates load data 53 containing the load average value and date information, and stores the load data 53 in the storage part 32. The storage part 32 cumulatively stores also a plurality of pieces of load data 53 concerning a plurality of load average values of the past until the day before.

Figure 4:
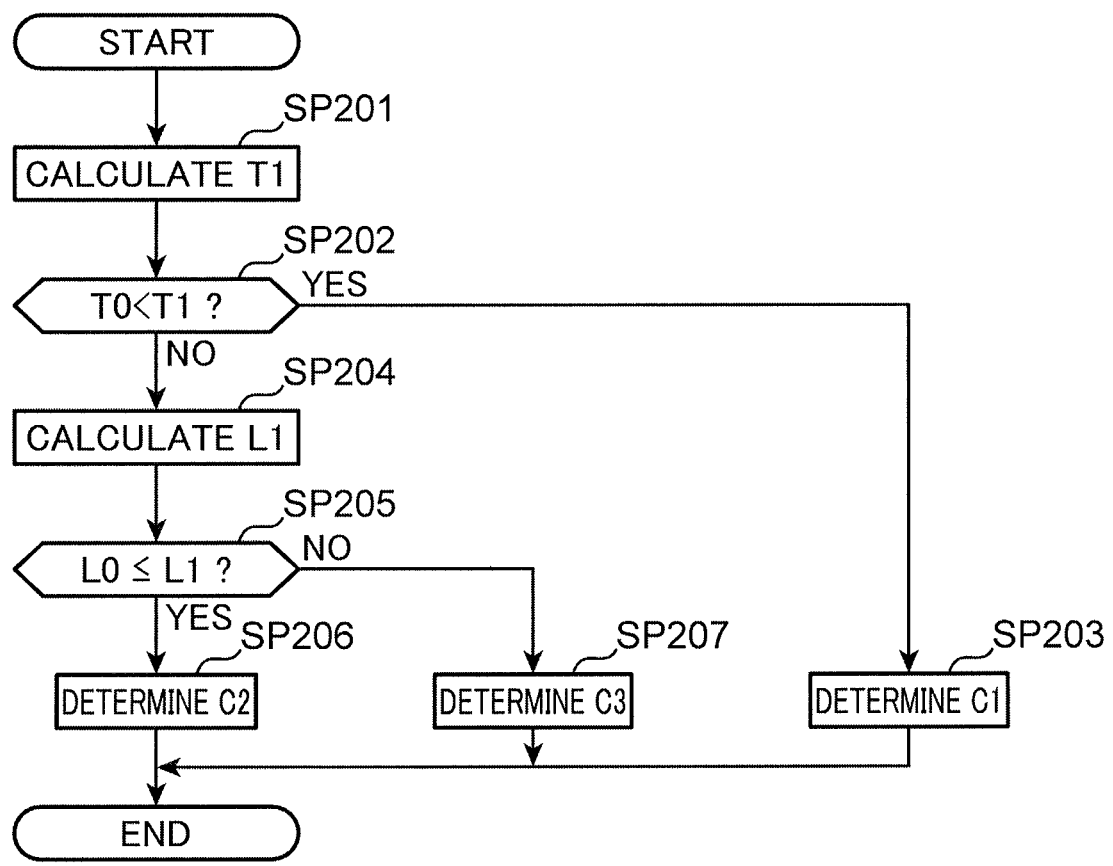
FIG. 4 is a flowchart showing a first exemplary process executed by the control part to determine a health condition of a subject.

FIG. 4 is a flowchart showing a first exemplary process executed by the control part 31 to determine a health condition of the subject.

First, in Step SP201, the calculation section 42 reads pieces of time data 52 concerning a predetermined period (e.g., the most recent full week or the most recent full month) of the past until the day before from the storage part 32, and calculates an average value of consumed time periods represented by the pieces of time data 52 to thereby obtain a reference consumed time period T1.

Thereafter, in Step SP202, the determination section 43 reads the time data 52 of the current day from the storage part 32, and determines whether the consumed time period of the current day TO represented by the time data 52 of the current day is shorter than the reference consumed time period T1.

When the consumed time period of the current day TO is shorter than the reference consumed time period T1 (Step SP202: YES), thereafter, in Step SP203, the determination section 43 determines that the subject is in a good health condition C1. In this case, the output section 44 outputs result data indicative of the condition C1 as a determination result by the determination section 43, and the communication part 33 sends the result data to the display device 22. The display device 22, which receives the result data indicative of the condition C1, displays on a screen a graphic or a text message indicative of the good health condition on that day. A way of notifying the user about a determination result may be an output of a voice from a speaker or the like in place of the display on the screen (the same applies hereinafter).

When the consumed time period of the current day TO is equal to or longer than the reference consumed time period T1 (Step SP202: NO), thereafter, in Step SP204, the calculation section 42 reads pieces of load data 53 concerning a predetermined period (e.g., the most recent full week or the most recent full month) of the past until the day before from the storage part 32, and calculates an average value of the load average values represented by the pieces of load data 53 to thereby obtain a reference load average value L1.

Thereafter, in Step SP205, the determination section 43 reads the load data 53 of the current day from the storage part 32, and determines whether the load average value of the current day L0 represented by the load data 53 of the current day is equal to or smaller than the reference load average value L1.

When the load average value of the current day L0 is equal to or smaller than the reference load average value L1 (Step SP205: YES), thereafter, in Step SP206, the determination section 43 determines that the subject is in a relatively poor health condition C2. In this case, the output section 44 outputs result data indicative of the condition C2 as a determination result by the determination section 43, and the communication part 33 sends the result data to the display device 22. The display device 22, which receives the result data indicative of the condition C2, displays on the screen a graphic or a text message that indicates the relatively poor health condition on that day.

When the load average value of the current day L0 is greater than the reference load average value L1 (Step SP205: NO), thereafter, in Step SP207, the determination section 43 determines that the subject is in a poor health condition C3. In this case, the output section 44 outputs result data indicative of the condition C3 as a determination result by the determination section 43, and the communication part 33 sends the result data to the display device 22. The display device 22, which receives the result data indicative of the condition C3, displays on the screen a graphic or a text message that indicates the poor health condition on that day.

Figure 5:
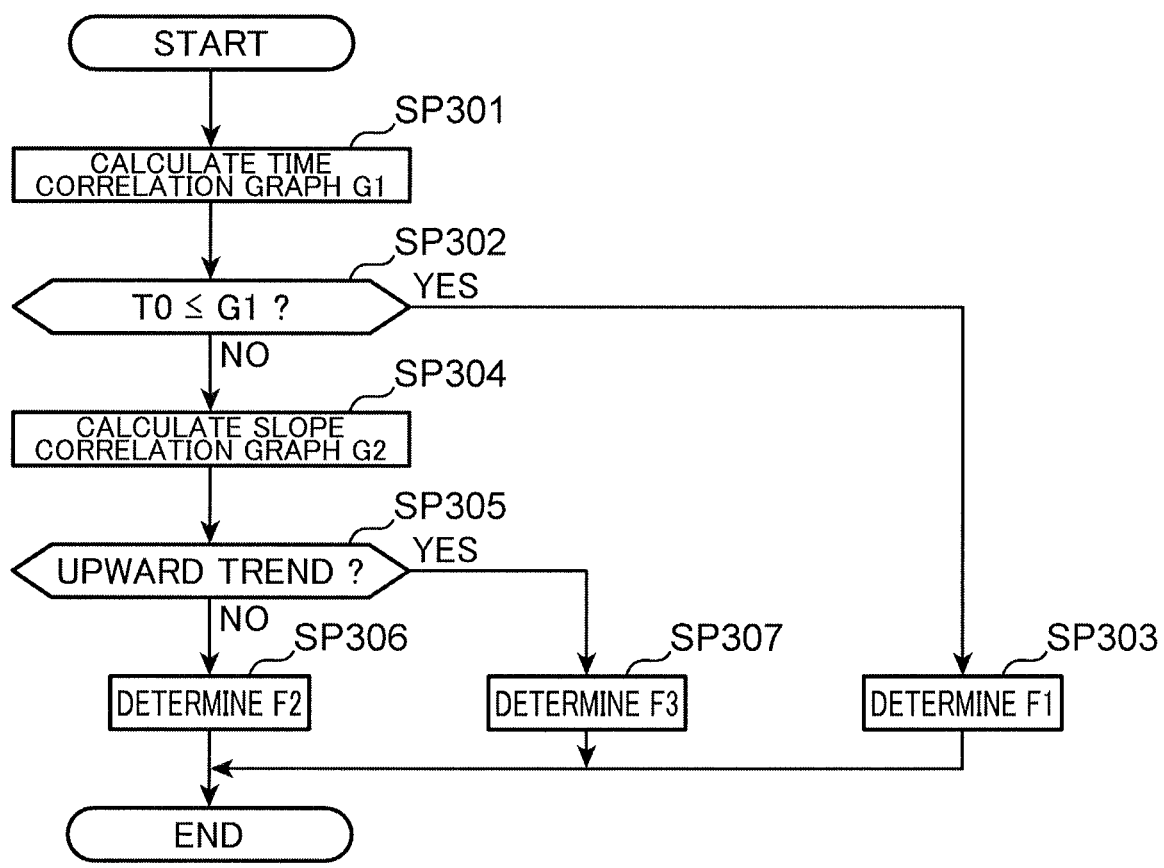
FIG. 5 is a flowchart showing a second exemplary process executed by the control part to determine a health condition of the subject.

FIG. 5 is a flowchart showing a second example of process executed by the control part 31 to determine a health condition of the subject.

Figure 6:
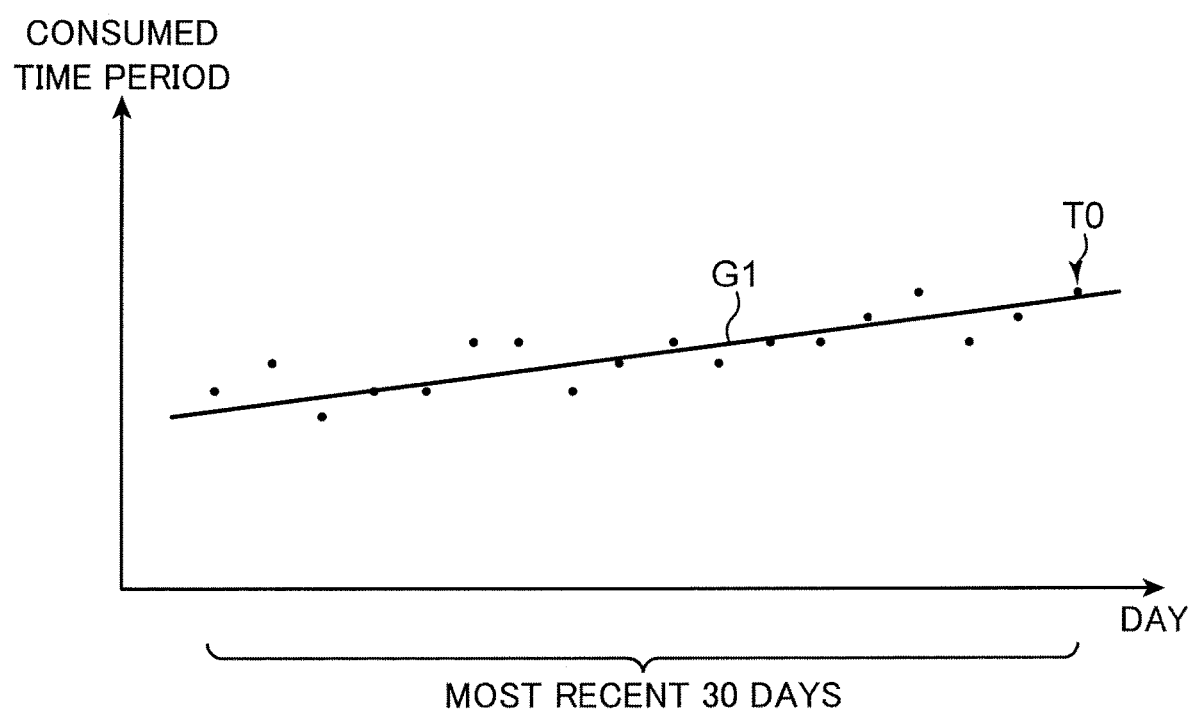
FIG. 6 shows an exemplary time correlation graph.

First, in Step SP301, the calculation section 42 reads pieces of time data 52 concerning the most recent predetermined period (e.g., 30 days) including the current day from the storage part 32, and applies a desired approximate straight line derivation algorithm, e.g., the least square method, to consumed time periods represented by the pieces of time data 52. Accordingly, the calculation section 42 calculates a time correlation graph G1 representing a change of the consumed time periods with respect to a time series on the basis of the pieces of time data 52 of the current day and the past. FIG. 6 is an exemplary time correlation graph G1 calculated about consumed time periods of the most recent 30 days. The calculation section 42 generates slope data 54 containing a slope value of a straight line of the time correlation graph G1 and date information, and stores in the storage part 32 as the slope data 54 of the current day. The storage part 32 cumulatively stores also a plurality of pieces of slope data 54 concerning a plurality of slope values of the past until the day before.

Thereafter, in Step SP302, the determination section 43 determines whether the consumed time period of the current day TO represented by the time data 52 of the current day is equal to or smaller than an estimated value of the current day represented as a value on the time correlation graph G1.

When the consumed time period of the current day TO is equal to or smaller than the estimated value of the current day (Step SP302: YES), thereafter, in Step SP303, the determination section 43 determines that the subject is in a robust health condition F1. In this case, the output section 44 outputs result data indicative of the condition F1 as a determination result by the determination section 43, and the communication part 33 sends the result data to the display device 22. The display device 22, which receives the result data indicative of the condition F1, displays on the screen a graphic or a text message indicative of the robust health condition on that day.

Figure 7:
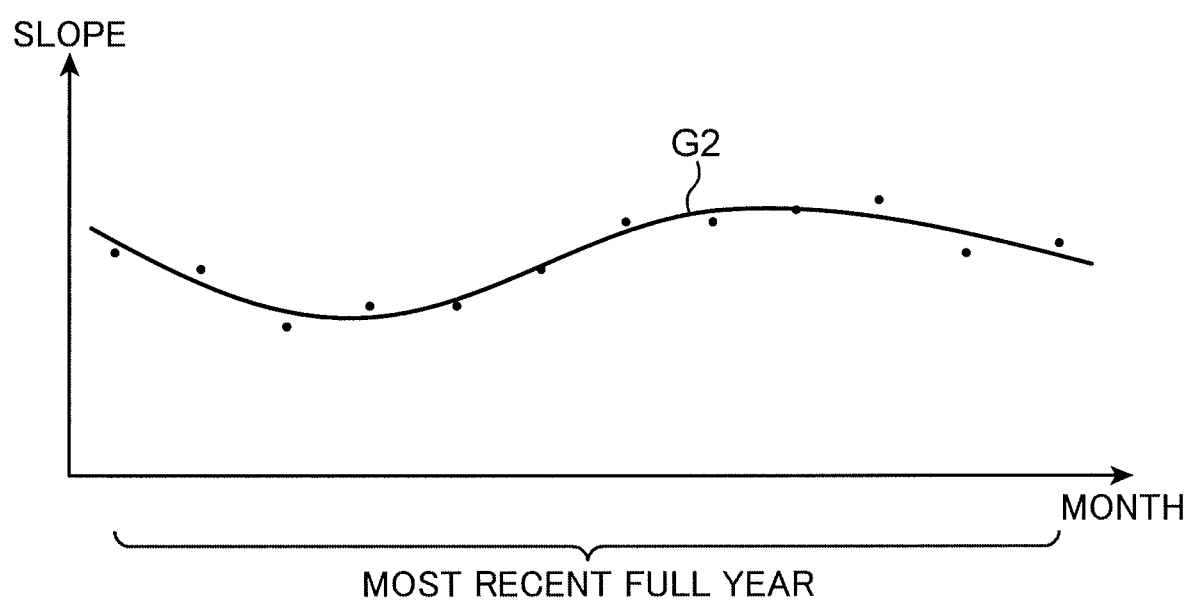
FIG. 7 shows an exemplary slope correlation graph.

When the consumed time period of the current day TO is greater than the estimated value of the current day (Step SP302: NO), thereafter, in Step SP304, the calculation section 42 reads pieces of slope data 54 concerning the most recent predetermined period (e.g., a year) including the current day from the storage part 32, and applies a desired approximate curve derivation algorithm, e.g., the Cosinor method, to slope values represented by the pieces of slope data 54. Accordingly, the calculation section 42 calculates a slope correlation graph G2 representing a change of the slope values with respect to a time series on the basis of the pieces of slope data 54 of the current day and the past. FIG. 7 shows an exemplary slope correlation graph G2 calculated about the slope values of the most recent full year. As shown in the example of FIG. 7, the calculation section 42 may monthly (or weekly) average slope values of the most recent full year to obtain an average value about each month (or each week), and calculate a slope correlation graph G2 on the basis of the average values.

Thereafter, in Step SP305, the determination section 43 determines whether the slope correlation graph G2 shows an upward trend (i.e., a trend according to which a slope value is smaller as the data is earlier and greater as the data is more recent).

When the slope correlation graph G2 does not show an upward trend (Step SP305: NO), for example, when the slope correlation graph G2 shows a downward trend or a cyclicity, thereafter, in Step SP306, the determination section 43 determines that the subject is in a condition F2 with a low probability of frailty (an intermediate state between a robust state and a care-requiring state). In this case, the output section 44 outputs result data indicative of the condition F2 as a determination result by the determination section 43, and the communication part 33 sends the result data to the display device 22. The display device 22, which receives the result data indicative of the condition F2, displays on the screen a graphic or a text message indicative of the low probability of frailty.

When the slope correlation graph G2 shows an upward trend (Step SP305: YES), thereafter, in Step SP307, the determination section 43 determines that the subject is in a condition F3 with a high probability of frailty. In this case, the output section 44 outputs result data indicative of the condition F3 as a determination result by the determination section 43, and the communication part 33 sends the result data to the display device 22. The display device 22, which receives the result data indicative of the condition F3, displays on the screen a graphic or a text message indicative of the high probability of frailty and a recommendation for an examination in a medical institution.

In the description above, the determination section 43 determines the probability of frailty depending on whether the slope correlation graph G2 shows an upward trend or not. However, another determination algorithm may be used. For example, the server device 21 collects pieces of slope data 54 concerning many users from a management device 11 of each user via a communication network 20. Many users include various users with different attributes, e.g., ages, genders, occupations, and residences, and includes users who are frail and users who are not frail. The server device 21 collects also these pieces of attribute information and frailty information from a management device 11 of each user via a communication network 20. The server device 21 creates a determination model for determining the probability of frailty using these pieces of information collected from the management devices 11 of many users according to Deep Learning, e.g., Neural Network. The server device 21 sends the created determination model to the management devices 11 via the communication network 20. Each of the management devices 11 determines the probability of frailty using the determination model on the basis of attribute information of each subject and slope data 54.

As described above, in the health condition determination system 100 according to this embodiment, a health condition of the subject is determined on the basis of a time period consumed by the subject to walk for the first time after the waking from the uppermost step (the one end step) to the lowermost step (the other end step) of the stair 6. The measurement is performed about the first walking after the waking, i.e., a daily activity repeated every day in a substantially fixed time period and almost in an unconscious manner mentally and physically. This makes it possible to eliminate factors variable independently of a health condition of the subject, consequently improving the determination accuracy of the health condition. Generally, there is no branch path or place to stop by along a stair 6. Limiting the measurement location of the walking time period to the stair 6 makes it possible to eliminate a factor of a path selection, which varies independently of a health condition of the subject, consequently improving the determination accuracy of the health condition. What is measured here is the first stair walking after the waking, which is a definite action in a daily life. This can reduce the amount of data to be processed by the management device 11, consequently reducing the process load entailed by the determination of the health condition.

Further, in the health condition determination system 100 according to this embodiment, not only a time period consumed by the subject to walk the stair 6 but also a load average value applied to the handrail 7 in that time period is used to determine a health condition of the subject. Therefore, the determination accuracy can be further improved.

Additionally, in the health condition determination system 100 according to this embodiment, a health condition is determined on the basis of a time correlation graph (the first correlation graph) G1 representing a change of the time data 52 with respect to a time series. Therefore, a health condition of the subject on the current day can be determined easily and at a high accuracy.

Further, in the health condition determination system 100 according to this embodiment, a probability that the subject is frail can be determined easily and at a high accuracy on the basis of a slope correlation graph (the second correlation graph) G2 representing a change of the slope data 54 with respect to a time series.

Further, in the health condition determination system 100 according to this embodiment, a movement of the subject from the bed 2 to the landing 5 is detected by a group of sensors including the bed leaving sensor 13, the open/close sensor 14, and the human sensing sensors 15, 16. This makes it possible to reliably determine that the stair walking to be measured is the first stair walking by the subject after the waking.

Features of the embodiment described above are summarized hereinafter.

A health condition determination system according to an aspect of the present invention is a health condition determination system for determining a health condition of a subject living in a housing provided with a stair, and includes: a first sensor that detects waking of the subject and outputs first data indicative of a result of the detection; a second sensor that detects the subject staying on one end step of the stair and outputs second data indicative of a result of the detection; a third sensor that detects the subject staying on the other end step of the stair and outputs third data indicative of a result of the detection; and a management device that is communicable with the first sensor, the second sensor, and the third sensor. The management device includes an acquisition part that acquires the first data, the second data, and the third data, a calculation part that calculates, on the basis of the first data, the second data, and the third data acquired by the acquisition part, a period of time consumed for a first walking of the subject after the waking from the one end step to the other end step of the stair, and outputs time data indicative of the period of time, a storage part that stores a plurality of pieces of time data of a past, a determination part that determines a health condition of the subject on a current day on the basis of the time data of the current day and the pieces of time data of the past, and an output part that outputs a determination result of the determination part.

In this configuration, a health condition of the subject is determined on the basis of a period of time consumed by the subject to walk from the one end step to the other end step of the stair for the first time after the waking. The measurement is performed about the first walking after the waking, i.e., a daily activity repeated every day in a substantially fixed time period and almost in an unconscious manner mentally and physically. This makes it possible to eliminate factors variable independently of a health condition of the subject, consequently improving the determination accuracy of the health condition. Generally, there is no branch path or place to stop by along a stair. Limiting the measurement location of the walking time period to the stair makes it possible to eliminate a factor of a path selection, which varies independently of a health condition of the subject, consequently improving the determination accuracy of the health condition. What is measured here is the first stair walking after the waking, which is a definite action in a daily life. This can reduce the amount of data to be processed by the management device, consequently reducing the process load entailed by the determination of the health condition.

In the above configuration, a fourth sensor that detects a load applied to a handrail of the stair by the subject and outputs fourth data indicative of a result of the detection may be further provided, the acquisition part may further acquire the fourth data, the calculation part may further calculate, on the basis of the fourth data acquired by the acquisition part, an average value of load applied to the handrail by the subject in the first walking after the waking from the one end step to the other end step of the stair, and output load data indicative of the load average value, the storage part may further store a plurality of pieces of load data of the past, and the determination part may determine a health condition of the subject on the current day on the basis of the time data and the load data of the current day and the pieces of time data and the pieces of load data of the past.

In this configuration, not only a period of time consumed by the subject when walking the stair but also an average value of load applied to the handrail in that period is used to determine a health condition of the subject. Therefore, the determination accuracy can be further improved.

In the above configuration, the calculation part may further calculate a first correlation graph representing a change of the time data with respect to a time series on the basis of the pieces of time data of the past, and the determination part may determine a health condition of the subject on the current day on the basis of the time data of the current day and the first correlation graph.

In this configuration, a health condition is determined on the basis of the first correlation graph that represents a change of the time data with respect to a time series. Therefore, a health condition of the subject on the current day can be determined easily and at a high accuracy.

In the above configuration, the calculation part may further calculate a slope value of the first correlation graph, and outputs slope data indicative of the slope value, the storage part may further store a plurality of pieces of slope data of the past, the calculation part may further calculate a second correlation graph representing a change of the slope data with respect to a time series on the basis of the pieces of slope data of the past, and the determination part may further determine a probability that the subject is frail on the basis of the second correlation graph.

In this configuration, a probability that the subject is frail can be determined easily and at a high accuracy on the basis of the second correlation graph that represents a change of the slope data with respect to a time series.

In the above configuration, a group of sensors that detects a movement of the subject from a sleeping position of the subject to a position immediately before the one end step may be further provided.

In this configuration, a movement of the subject from the sleeping position of the subject to the position immediately before the one end step is detected by a group of sensors. Therefore, it is possible to reliably determine that the stair walking to be measured is the first stair walking by the subject after the waking.

A housing according to an aspect of the present invention includes a stair and the health condition determination system according to the above aspect.

A management device according to an aspect of the present invention is to be provided in a health condition determination system that determines a health condition of a subject living in a housing provided with a stair. The health condition determination system includes a first sensor that detects waking of the subject and outputs first data indicative of a result of the detection, a second sensor that detects the subject staying on one end step of the stair and outputs second data indicative of a result of the detection, a third sensor that detects the subject staying on the other end step of the stair and outputs third data indicative of a result of the detection. The management device is communicable with the first sensor, the second sensor, and the third sensor. The management device includes an acquisition part that acquires the first data, the second data, and the third data, a calculation part that calculates, on the basis of the first data, the second data, and the third data acquired by the acquisition part, a period of time consumed for a first walking of the subject after the waking from the one end step to the other end step of the stair, and outputs time data indicative of the period of time, a storage part that stores a plurality of pieces of time data of a past, a determination part that determines a health condition of the subject on a current day on the basis of the time data of the current day and the pieces of time data of the past, and an output part that outputs a determination result of the determination part.

A program according to an aspect of the present invention causes a computer to function as a management device provided in a health condition determination system that determines a health condition of a subject living in a housing provided with a stair. The health condition determination system includes a first sensor that detects waking of the subject and outputs first data indicative of a result of the detection, a second sensor that detects the subject staying on one end step of the stair and outputs second data indicative of a result of the detection, and a third sensor that detects the subject staying on the other end step of the stair and outputs third data indicative of a result of the detection. The management device is communicable with the first sensor, the second sensor, and the third sensor. The program causes the computer to function as an acquisition means that acquires the first data, the second data, and the third data, a calculation means that calculates, on the basis of the first data, the second data, and the third data acquired by the acquisition means, a period of time consumed for a first walking of the subject after the waking from the one end step to the other end step of the stair, and outputs time data indicative of the period of time, a determination means that determines a health condition of the subject on a current day on the basis of the time data of the current day and the pieces of time data of the past, and an output means that outputs a determination result of the determination means.

A health condition determination method according to an aspect of the present invention is a determination method for determining a health condition of a subject living in a housing provided with a stair, and includes detecting waking of the subject by a first sensor to output first data indicative of a result of the detection, detecting the subject staying on one end step of the stair by a second sensor to output second data indicative of a result of the detection, detecting the subject staying on the other end step of the stair to output third data indicative of a result of the detection, allowing a management device to acquire the first data, the second data, and the third data, calculate, on the basis of the first data, the second data, and the third data that are acquired, a period of time consumed for a first walking of the subject after the waking from the one end step to the other end step of the stair, and output time data indicative of the period of time, store a plurality of pieces of time data of a past, determine a health condition of the subject on a current day on the basis of the time data of the current day and the pieces of time data of the past, and output a determination result.

In these aspects, a health condition of the subject is determined on the basis of a period of time consumed by the subject to walk from the one end step to the other end step of the stair for the first time after the waking. The measurement is performed about the first walking after the waking, i.e., a daily activity repeated every day in a substantially fixed time period and almost in an unconscious manner mentally and physically. This makes it possible to eliminate factors variable independently of a health condition of the subject, consequently improving the determination accuracy of the health condition. Generally, there is no branch path or place to stop by along a stair. Limiting the measurement location of the walking time period to the stair makes it possible to eliminate factors variable independently of a health condition of the subject, consequently improving the determination accuracy of the health condition. What is measured here is the first stair walking after the waking, which is a definite action in a daily life. This can reduce the amount of data to be processed by the management device, consequently reducing the process load entailed by the determination of the health condition.

The invention claimed is:

1. A health condition determination system for determining a health condition of a subject living in a housing provided with a stair, comprising:
   a first sensor that detects waking of the subject and outputs first data indicative of a result of the detection;
   a second sensor that detects the subject staying on one end step of the stair and outputs second data indicative of a result of the detection;
   a third sensor that detects the subject staying on the other end step of the stair and outputs third data indicative of a result of the detection; and
   a management device that is communicable with the first sensor, the second sensor, and the third sensor, wherein
   the management device includes
      an acquisition part that acquires the first data, the second data, and the third data;
      a calculation part that calculates, on the basis of the first data, the second data, and the third data acquired by the acquisition part, a period of time consumed for a first walking of the subject after the waking from the one end step to the other end step of the stair, and outputs time data indicative of the period of time;

a storage part that stores a plurality of pieces of time data of a past;

a determination part that determines a health condition of the subject on a current day on the basis of the time data of the current day and the pieces of time data of the past; and an output part that outputs a determination result of the determination part.

2. The health condition determination system according to claim 1, further comprising:

a fourth sensor that detects a load applied to a handrail of the stair by the subject and outputs fourth data indicative of a result of the detection, wherein the acquisition part further acquires the fourth data, the calculation part further calculates, on the basis of the fourth data acquired by the acquisition part, a load value applied to the handrail by the subject in the first walking after the waking from the one end step to the other end step of the stair, and outputs load data indicative of the load value, the storage part further stores a plurality of pieces of load data of the past, and the determination part determines a health condition of the subject on the current day on the basis of the time data and the load data of the current day and the pieces of time data and the pieces of load data of the past.

3. The health condition determination system according to claim 1, wherein the calculation part further calculates a first correlation graph representing a change of the time data with respect to a time series on the basis of the pieces of time data of the past, and the determination part determines a health condition of the subject on the current day on the basis of the time data of the current day and the first correlation graph.

4. The health condition determination system according to claim 3, wherein the calculation part further calculates a slope value of the first correlation graph, and outputs slope data indicative of the slope value, the storage part further stores a plurality of pieces of slope data of the past, the calculation part further calculates a second correlation graph representing a change of the slope data with respect to a time series on the basis of the pieces of slope data of the past, and the determination part further determines a probability that the subject is frail on the basis of the second correlation graph.

5. The health condition determination system according to claim 1, further comprising:

a group of sensors that detects a movement of the subject from a sleeping position of the subject to a position immediately before the one end step.

6. A management device to be provided in a health condition determination system that determines a health condition of a subject living in a housing provided with a stair and includes:

a first sensor that detects waking of the subject and outputs first data indicative of a result of the detection;

a second sensor that detects the subject staying on one end step of the stair and outputs second data indicative of a result of the detection;

a third sensor that detects the subject staying on the other end step of the stair and outputs third data indicative of a result of the detection, the management device that is communicable with the first sensor, the second sensor, and the third sensor, the management device, comprising:

an acquisition part that acquires the first data, the second data, and the third data, a calculation part that calculates, on the basis of the first data, the second data, and the third data acquired by the acquisition part, a period of time consumed for a first walking of the subject after the waking from the one end step to the other end step of the stair, and outputs time data indicative of the period of time;

a storage part that stores a plurality of pieces of time data of a past;

a determination part that determines a health condition of the subject on a current day on the basis of the time data of the current day and the pieces of time data of the past; and an output part that outputs a determination result of the determination part.

7. A health condition determination method for determining a health condition of a subject living in a housing provided with a stair, comprising:

detecting waking of the subject by a first sensor to output first data indicative of a result of the detection, detecting the subject staying on one end step of the stair by a second sensor to output second data indicative of a result of the detection;

detecting the subject staying on the other end step of the stair by a third sensor to output third data indicative of a result of the detection, allowing a management device to:

acquire the first data, the second data, and the third data;

calculate, on the basis of the first data, the second data, and the third data that are acquired, a period of time consumed for a first walking of the subject after the waking from the one end step to the other end step of the stair, and output time data indicative of the period of time;

store a plurality of pieces of time data of a past;

determine a health condition of the subject on a current day on the basis of the time data of the current day and the pieces of time data of the past; and output a determination result.

* * * * *